United States Patent [19]
Eberlin

[11] Patent Number: 5,702,048
[45] Date of Patent: Dec. 30, 1997

[54] DEVICE FOR MICROANATOMOSIS OF BLOOD VESSELS

[76] Inventor: René Eberlin, 25, Avenue Jeandin, CH-1226 Thonex, Switzerland

[21] Appl. No.: 343,424
[22] PCT Filed: Mar. 18, 1994
[86] PCT No.: PCT/FR94/00302
  § 371 Date: Feb. 3, 1995
  § 102(e) Date: Feb. 3, 1995
[87] PCT Pub. No.: WO94/21181
  PCT Pub. Date: Sep. 29, 1994

[30] Foreign Application Priority Data

Mar. 18, 1993 [FR] France ................ 93 03337

[51] Int. Cl.⁶ ........................................ A61B 17/068
[52] U.S. Cl. ............... 227/177.1; 227/19; 227/175.1; 227/176.1; 606/143; 606/220
[58] Field of Search ................. 227/19, 175.1, 227/176.1, 177.1, 901; 606/142, 143, 219, 220

[56] References Cited

U.S. PATENT DOCUMENTS

| | | | |
|---|---|---|---|
| 3,232,089 | 2/1966 | Samuels et al. | 606/142 |
| 4,152,920 | 5/1979 | Green | 227/19 X |
| 4,299,224 | 11/1981 | Noiles | 227/19 X |
| 4,425,915 | 1/1984 | Ivanov | 227/19 X |
| 4,611,595 | 9/1986 | Klieman et al. | 606/143 |
| 4,657,019 | 4/1987 | Walsh et al. | 128/334 C |
| 4,762,260 | 8/1988 | Richards et al. | 227/19 |
| 4,809,685 | 3/1989 | Gwathmey et al. | 227/19 X |
| 4,821,942 | 4/1989 | Richards | 227/19 X |
| 4,887,601 | 12/1989 | Richards | 606/219 |
| 4,917,087 | 4/1990 | Walsh et al. | 606/153 |
| 4,930,674 | 6/1990 | Barak | 227/179.1 |
| 4,944,295 | 7/1990 | Gwathmey et al. | 227/176.1 |
| 4,944,443 | 7/1990 | Oddsen et al. | 227/19 |
| 4,969,591 | 11/1990 | Richards et al. | 227/177.1 |
| 4,979,954 | 12/1990 | Gwathmey et al. | 606/219 |
| 4,997,436 | 3/1991 | Oberlander | 227/901 X |
| 5,014,149 | 5/1991 | Nakao et al. | 227/901 X |
| 5,042,707 | 8/1991 | Taheri | 227/19 X |
| 5,049,152 | 9/1991 | Simon et al. | 606/143 |
| 5,207,692 | 5/1993 | Kraus et al. | 227/901 X |
| 5,222,961 | 6/1993 | Nakao et al. | 606/142 X |
| 5,234,447 | 8/1993 | Kaster et al. | 606/153 |
| 5,258,007 | 11/1993 | Spetzler et al. | 227/901 X |
| 5,290,299 | 3/1994 | Fain et al. | 606/142 |
| 5,304,183 | 4/1994 | Gourlay et al. | 227/901 X |
| 5,366,462 | 11/1994 | Kaster et al. | 606/153 |
| 5,382,253 | 1/1995 | Hogendijk | 227/901 X |
| 5,403,333 | 4/1995 | Kaster et al. | 606/151 |

FOREIGN PATENT DOCUMENTS

| | | |
|---|---|---|
| 0 503 271 | 9/1992 | European Pat. Off. |
| 2 006 021 | 5/1979 | United Kingdom |
| 2 162 782 | 2/1986 | United Kingdom |
| 2 181 356 | 4/1987 | United Kingdom |

Primary Examiner—Joseph J. Hall, III
Assistant Examiner—Jay A. Stelacone
Attorney, Agent, or Firm—McAulay Fisher Nissen Goldberg & Kiel, LLP

[57] ABSTRACT

A device for microanastomosis of blood vessels has a housing (1) provided with a gripper (3) for grasping and crimping staples (4, 5), housing (1) enclosing a mechanism for crimping staples (4, 5) by actuating the gripper (3). This mechanism has a control member (16) which is accessible from outside the housing (1), a staple magazine (33) and a mechanism for transferring a staple (4, 5) from the magazine to a position between the jaws of the gripper (3) which is likewise controlled by a member (9) accessible from outside the housing (1).

11 Claims, 16 Drawing Sheets

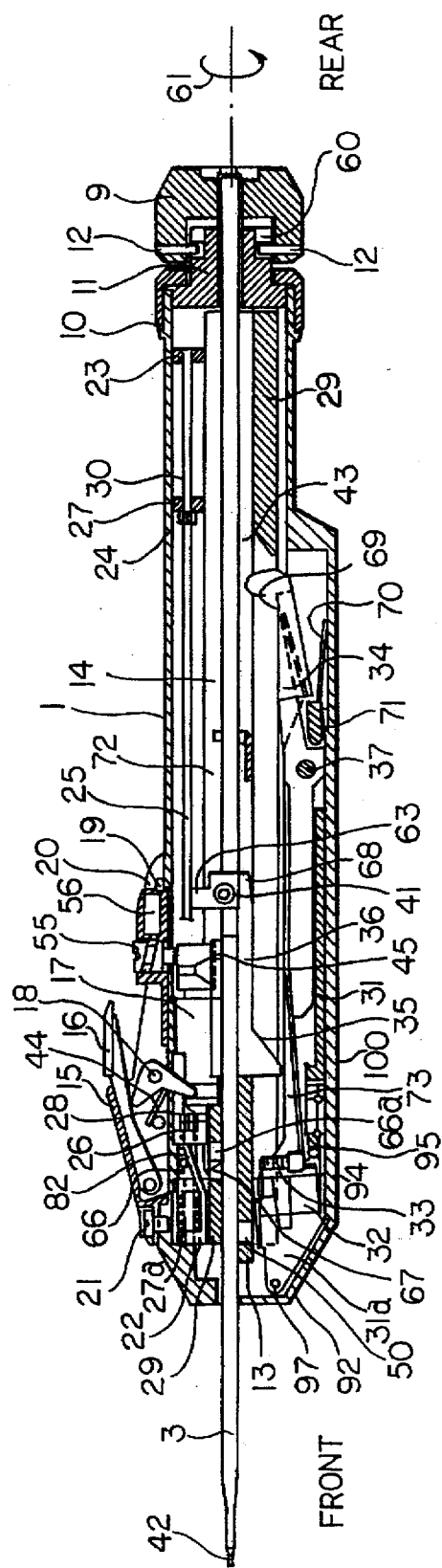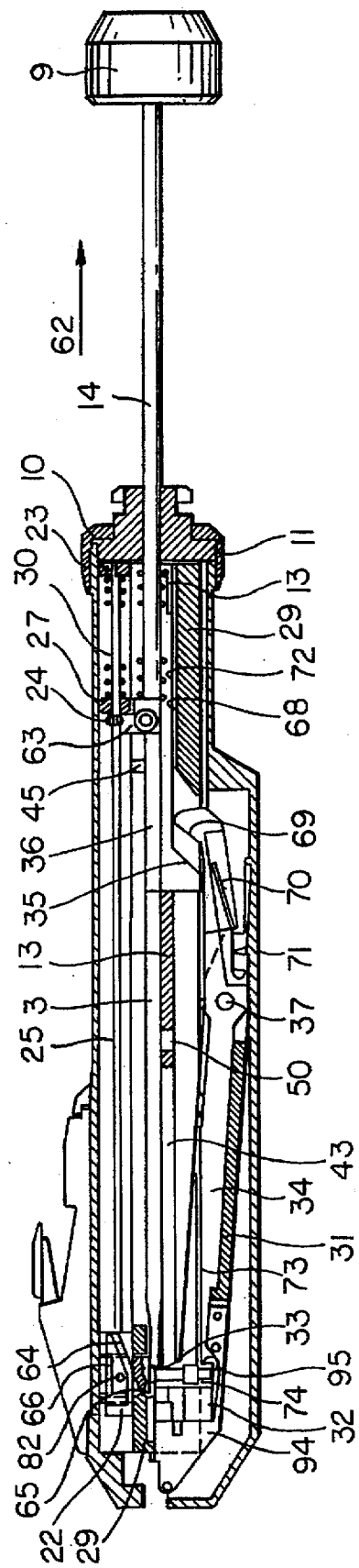

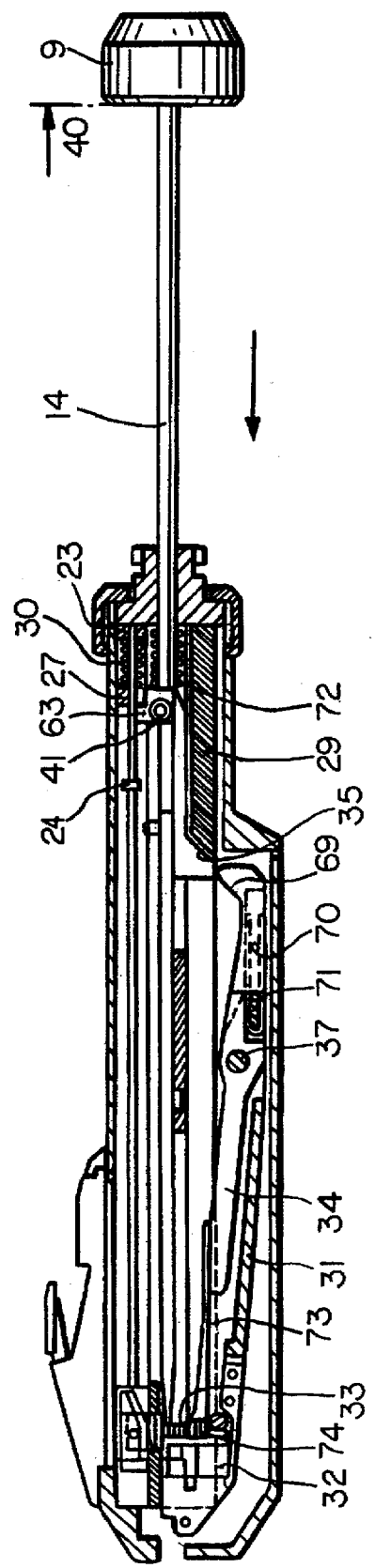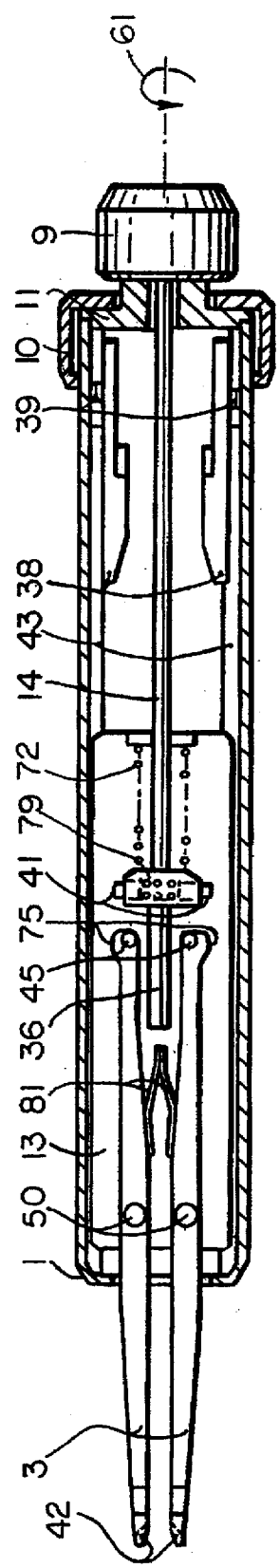

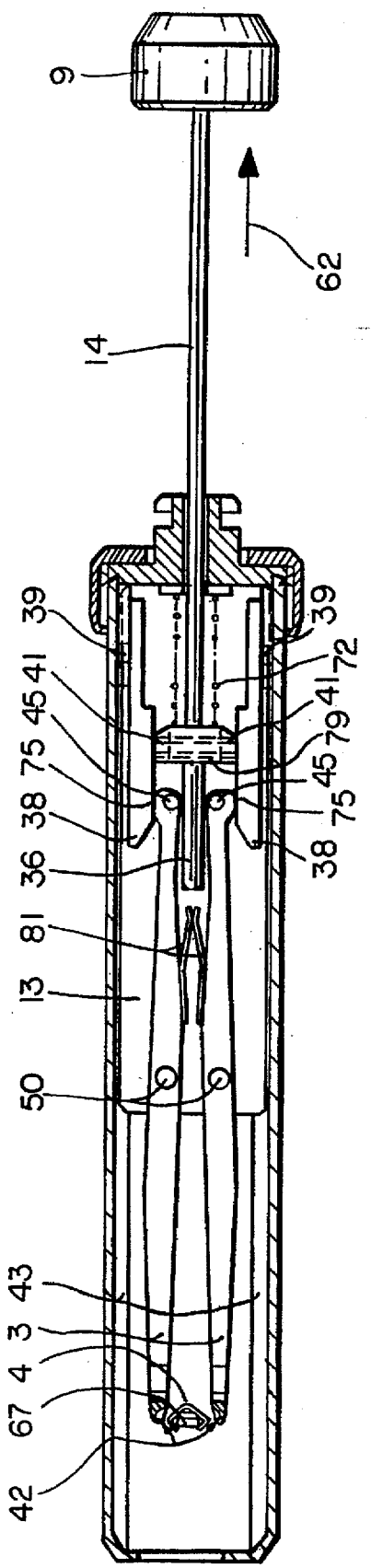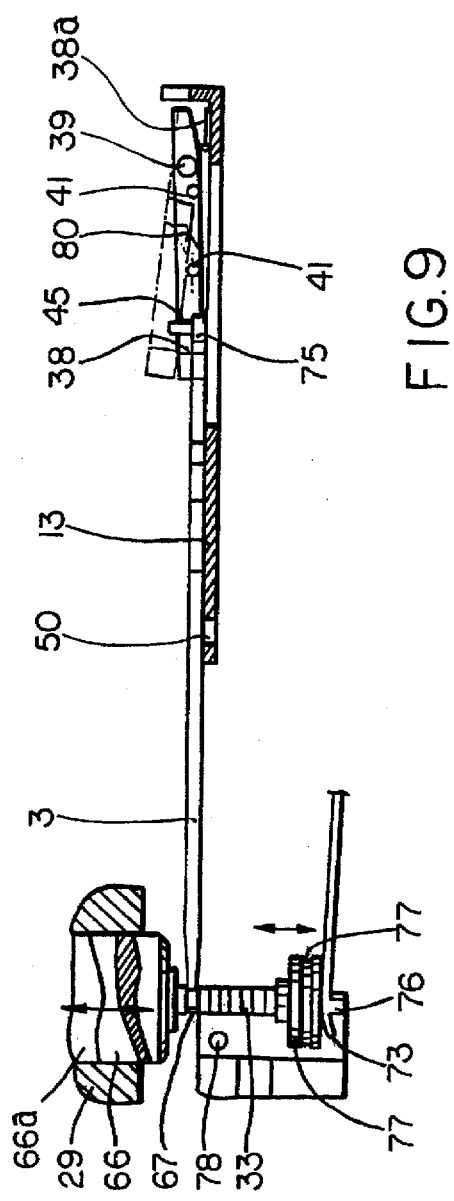
FIG. 8
FIG. 9

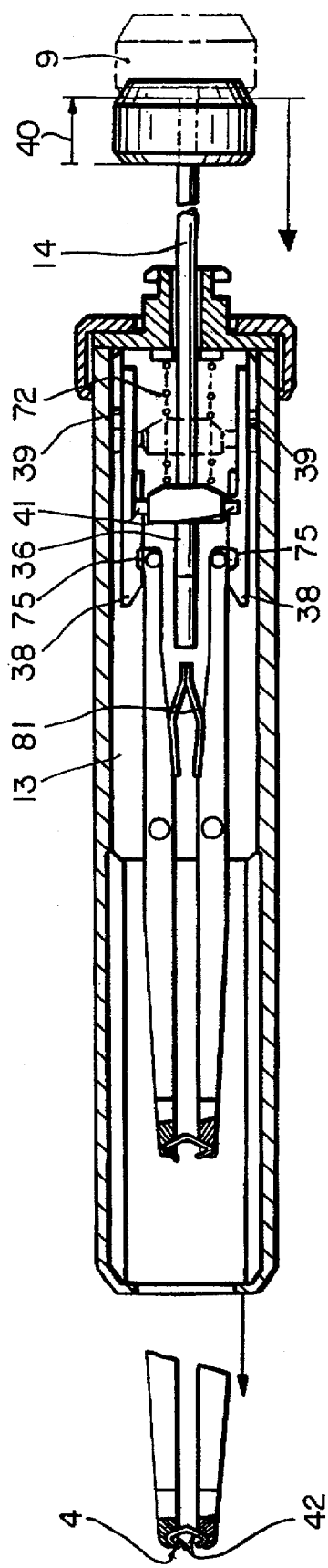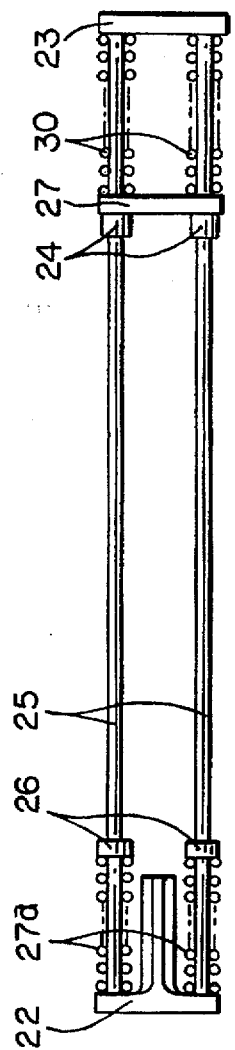
FIG.10
FIG.11

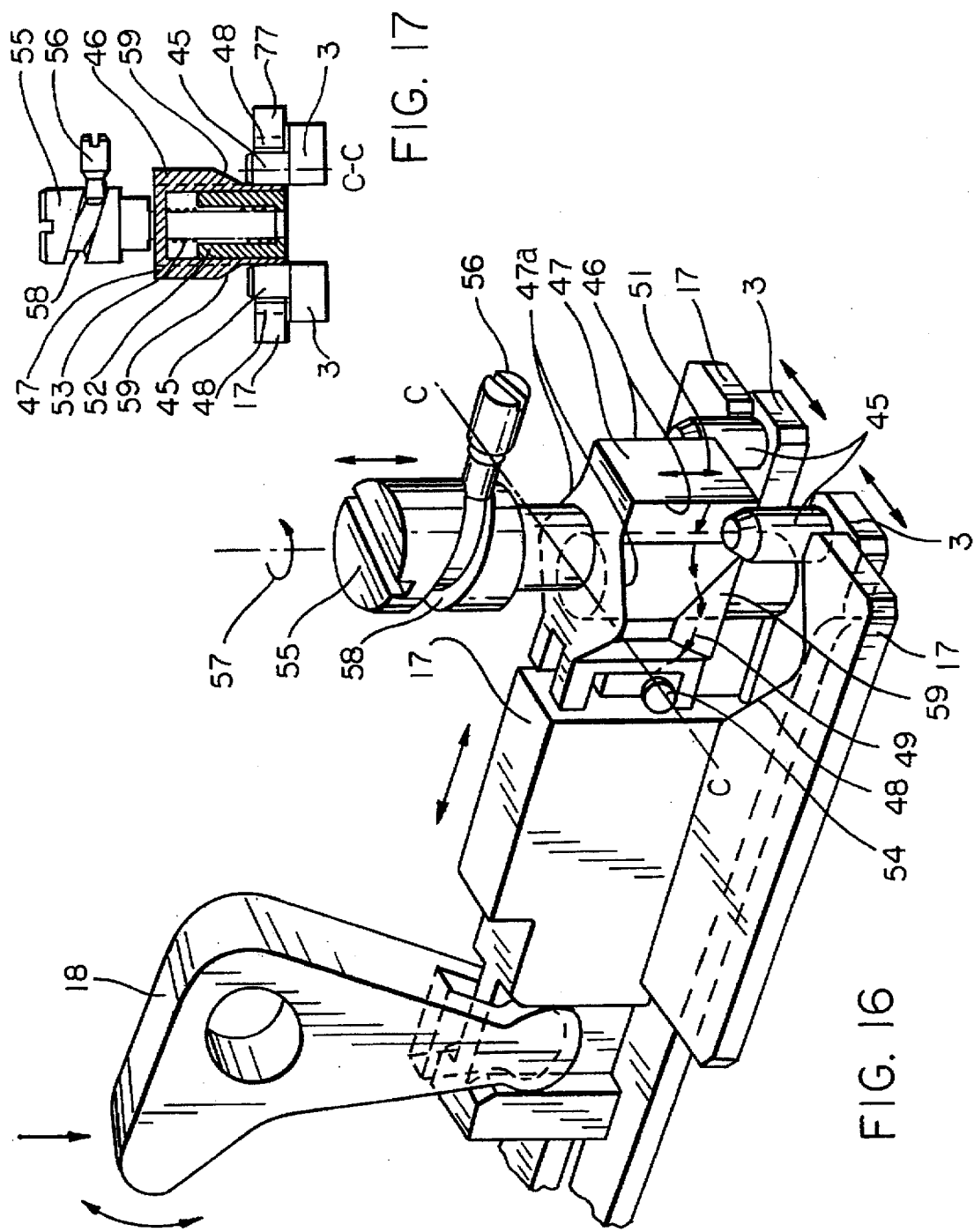

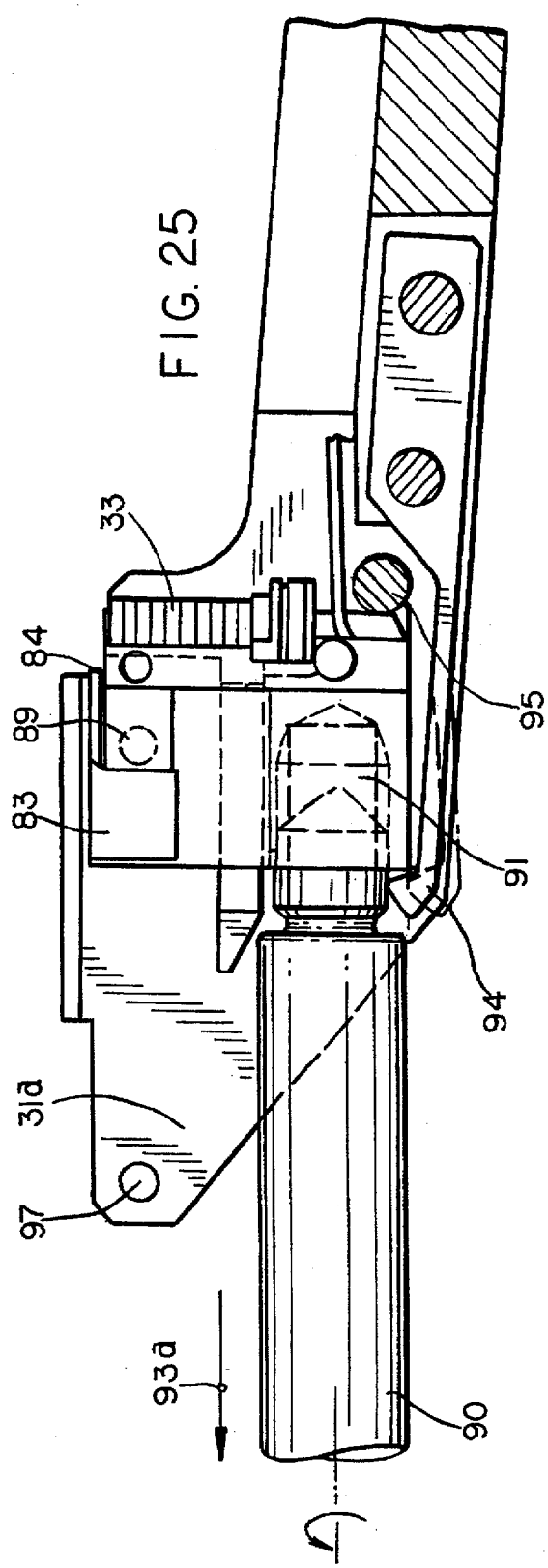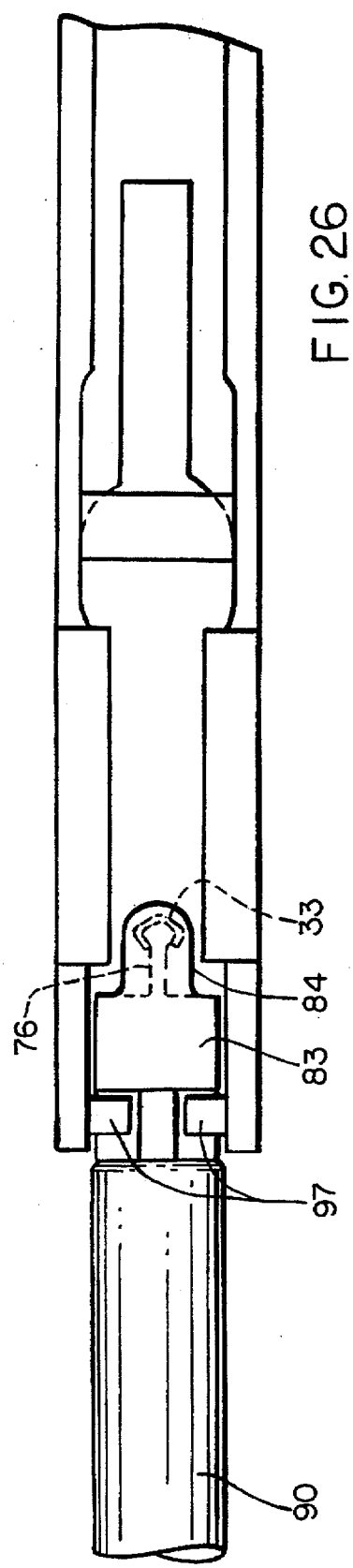

DEVICE FOR MICROANATOMOSIS OF BLOOD VESSELS

BACKGROUND OF THE INVENTION

1. Field of the Invention

Blood vessels are sutured in most cases using needles and nonabsorbable sutures. This technique is satisfactory for the most part, but principally for vascular surgery of large vessels, that is, vessels having a diameter greater than 3 mm. This technique is fast and reliable.

2. Description of the Prior Art

By contrast, in vascular microsurgery, i.e., for arteries and veins between 3 mm and 0.5 mm in diameter, this technique requires lengthy training in the laboratory because it relies on magnification instruments, lenses and particularly microscopes, microsurgical instruments and especially needles and very fine threads. Thus, clinical application of such vascular sutures on human patients is still at present subject to limitations: the lengthy training period, prolonged operating times with a minimum of fifteen minutes for each vascular suture and, finally, a moderately high risk of thrombosis.

Other techniques for vascular micro-sutures have been proposed over the years to mitigate these limitations:

The Nakayama ring suture which allows the two ends of the vessel to be joined by means of a male ring and female ring provided with barbs on which the vessel wall is everted.

The coupler developed more recently by the 3M company which utilizes the same principle.

Vascular anastomosis by laser.

Use of biological glues.

Vascular anastomosis with Nakayama's rings or couplers cannot be used for vessels less than one millimeter and can only be used for terminoterminal or end-to-end anastomoses. They have no practical use for terminolateral or end-to-side anastomoses.

The advantages of laser anastomosis are limited in that its use requires placement of at least three traditional sutures.

Anastomosis by biological adhesive presents the same disadvantages because of inadequate tensioning force to maintain contact between the two ends and due to the fact that associated stitches are also indispensable.

SUMMARY OF THE INVENTION

Therefore, the present invention proposes a new method for quick, simple and dependable vascular microanastomoses which does not have the limits and drawbacks of previous methods, as well as a gripper for implementing this method. The method and gripper are characterized by the features contained in the claims and in the following description.

The object of the present invention is a method for microanastomosis of blood vessels in particular, characterized in that the two ends of the vessel to be joined are placed end to end and the walls of the vessel which are placed end to end are joined in several places by bending or crimping a metallic micro-staple.

Another object of the invention is a device for carrying out this method having a housing which is provided with a gripper for grasping and crimping staples and contains a mechanism for crimping the staples by actuating the gripper, which mechanism has a control member which is accessible from outside the housing; a staple magazine and a mechanism for transferring a staple from the magazine to a position between the jaws of the gripper which is likewise controlled by a control member accessible from outside the housing.

BRIEF DESCRIPTION OF THE DRAWINGS

An embodiment form of the gripper according to the invention, the staples used by the gripper and the procedure for placing these staples are illustrated by way of example in the accompanying schematic drawings.

FIG. 3b shows a detail of a point of the staple shown in FIG. 3a;

FIGS. 4, 5, 6 show the gripper in three different operating positions in section along a plane of symmetry;

FIGS. 7, 8, 10 show sections along a plane perpendicular to the plane of symmetry of the gripper corresponding to the views shown in FIGS. 4, 5, 6, respectively;

FIG. 9 shows the gripper in partial section similar to FIGS. 4 to 6 with an enlarged view of the feed mechanism of the gripper with a staple;

FIG. 11 shows the horizontally displaceable part of a mechanism for placing a new staple in the arms of the gripper;

FIGS. 16 and 17 show a presetting mechanism for crimping the staple;

FIGS. 18 to 27 show a staple feed mechanism and the procedure for loading the feed mechanism.

DESCRIPTION OF THE PREFERRED EMBODIMENT

This novel method makes use of metal micro-staples for microanastomosis of vessels having a diameter between 3 mm and 0.5 mm. The shape of these staples is perfectly suited to microvascular anastomosis.

The material from which the staples are produced satisfies demands respecting flexibility and resistance to stretching. Further, these staples are made from biologically implantable metal conforming to AFNOR standards. They are inserted by means of an automatic gripper whose high-precision specifications necessitated in equal measure the conception and realization of a mechanism adapted to the small size of the staples, the flexibility of the body of the staples and the delicacy of their points. The chief advantages in favor of this novel technique consist in the speed and reliability with which anastomoses can be performed.

Figure 13:
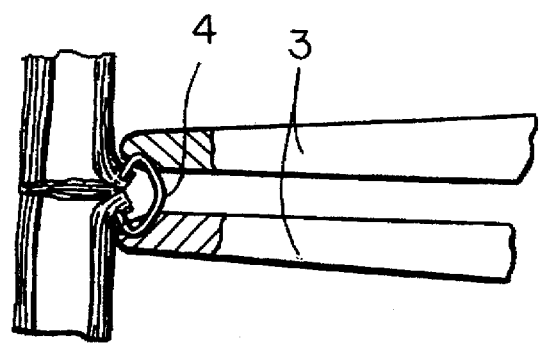
FIGS. 13 to 15 are schematic views showing the placement of a staple by means of the gripper.
Figure 14:
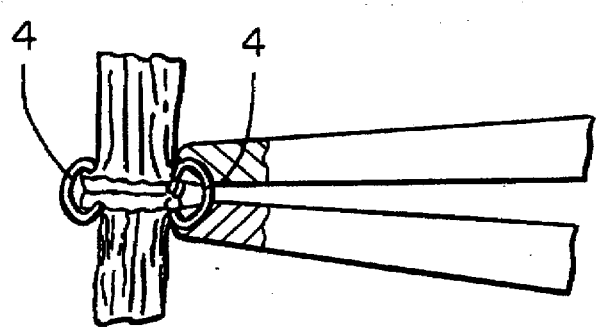
Figure 15:
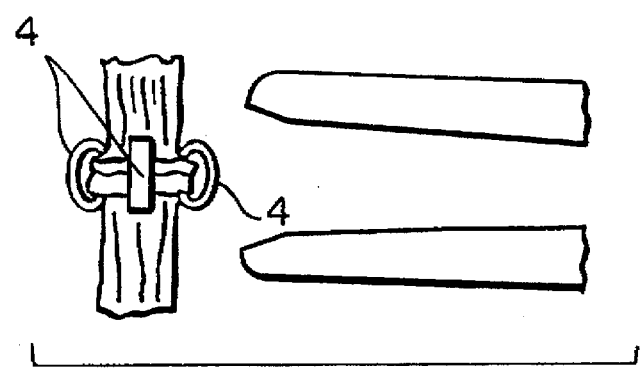

The principle of this novel anastomosis technique is explained in the description with reference to FIGS. 13 to 15.

Figure 3A:
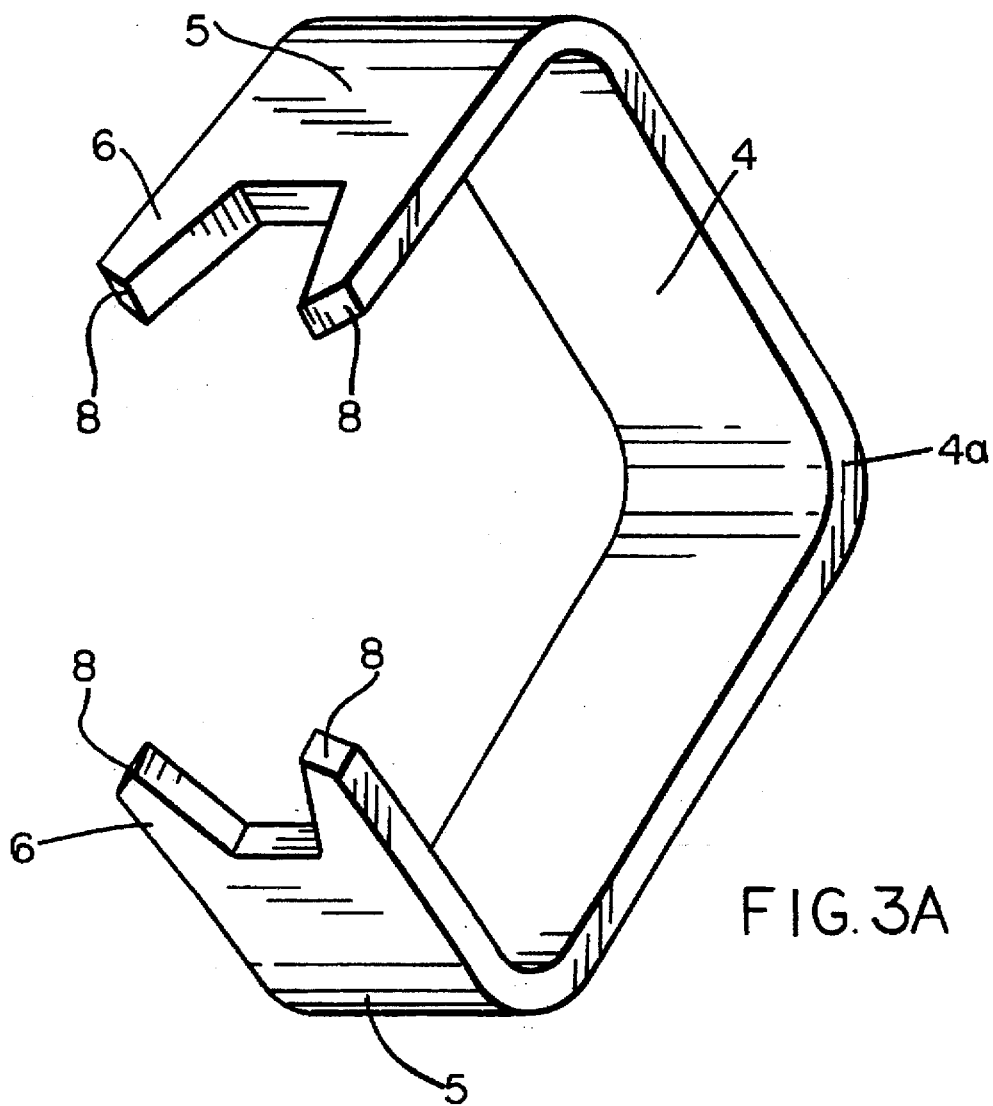
FIG. 3a is an enlarged view of a staple.
Figure 3B:
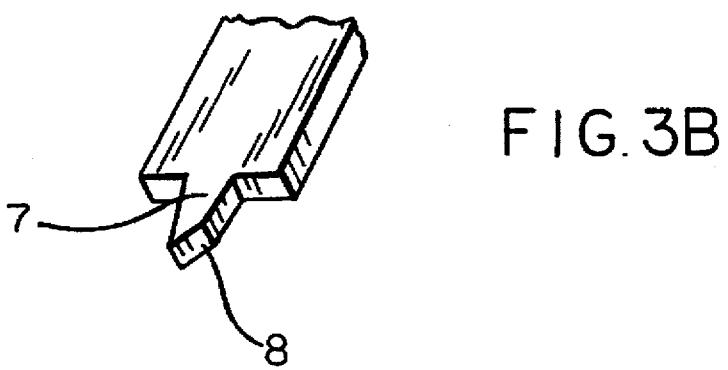

FIGS. 3a and 3b also show two possible embodiments of the staple. The gripper, its operation and use are described in the following.

The invention comprises a novel method for anastomosis and a staple designed to remain within the patient's body, suitable with respect to shape and construction for storage in magazines and adapted to requirements for handling and crimping by the mechanisms of a gripper specifically designed for placing this staple, this gripper likewise making up part of the invention.

The gripper which can easily be used under a microscope is provided with an interchangeable magazine containing a plurality of staples.

After attaching a staple, a new staple may be placed in the sockets provided at the ends of the arms of the gripper by a simple and quick operation of a knob arranged at the rear of the gripper.

The magazines are changed by means of a special spindle which is screwed into the magazine so that the magazine need not be handled and can thus maintain its sterilized condition.

Magazines whose store of staples has not been entirely depleted may be refilled and reused.

The crimping of the staples, i.e., the bending together of the claws and fastening of the staple on the suture to be performed, may be preset by means of a special button arranged on top of the gripper. When preset in this way, crimping does not depend on the movement and pressure exerted by the operator's index finger on the crimping lever provided at the upper front portion of the gripper.

At the end of this same movement, applying the same pressure with the index finger, the operator causes the arms of the gripper to spread apart, away from the staple inserted in the tissue so that the gripper may be withdrawn without the risk of tearing out the staple.

The staple is held in sockets provided at the end of the arms of the gripper and adapted to the shape of the staple. The considerable length of these arms facilitates the approach to the point of application of the staple. The staple may easily be fastened in the tissue by an operator of average skill. The crimping itself is effected very quickly taking only a few seconds. Speed and reliability of staple attachment are important factors for this type of procedure.

In the approach phase, the arms of the gripper are kept immobile by the internal mechanism. Accordingly, there is no danger of losing a staple above the operative field, which would be dangerous due to the very small dimensions of the staple.

The internal mechanisms of the gripper can easily be removed from the gripper manually by unscrewing a nut at the rear of the gripper and pulling on the end knob. These mechanisms may be disassembled easily by hand to permit thorough cleaning and sterilization. The gripper may be reused as desired.

Three sizes of staple may be used with the same gripper by changing the arms of the gripper, which can be done manually.

Three types of magazine are provided corresponding to each staple size. These magazines are also interchangeable.

Sterilization may be carried out at high temperatures or by gamma radiation. The gripper may be used without modification by either a left-handed or right-handed person. The gripper forms a rectilinear body. The sleeve 1 (FIG. 1) may be grasped by the operator in the manner of a pen. Grooved portions 2 are provided on either side of the sleeve 1 so that the gripper may be held more easily. Movable arms 3 project out of the sleeve at the front of the gripper. These arms 3 are capable of holding a micro-staple between their ends (FIGS. 2 and 3) so that the staple may be moved toward the parts to be sutured within the confined space of the operative field.

The micro-staple 4 (FIG. 3a) is characterized by a C-shape which can vary somewhat depending on the size of the staple and is formed by a central part 4a and two legs 5. It is produced, e.g., from a flat band of rectangular section. Provided at each end of the legs of the staple are pairs of claws 6 whose dimensions are very precise in spite of the very small dimensions of the staple (e.g.: 0.4 mm wide and 0.1 mm thick; the crimped staple could fit within a circle of roughly 1 mm diameter).

There may be two claws as in FIG. 3a, version 6 or a single claw as in FIG. 3b, version 7, the latter being a possible embodiment for the smallest micro-staple constructions (e.g., 0.08 mm thick and 0.25 mm wide in section).

The points of the claws are cut off along inclined planes 8 (FIGS. 3a and 3b) so that the end of the claw is not excessively sharp and delicate and accordingly not too cutting.

A knob 9 (FIG. 1) located at the rear of the gripper serves to control the reloading of a new staple in the ends of the arms 3. A nut 10 retains a back cover 11 which closes the sleeve (FIG. 4). This back cover contains a bayonet locking system in which the pins 12 of the knob 9 can engage (FIG. 4). This bayonet lock holds a drive plate 13 in position by the pressure of the knob 9 exerted on the rod 14 which is integral with the plate 13 (FIG. 4).

Figure 1:
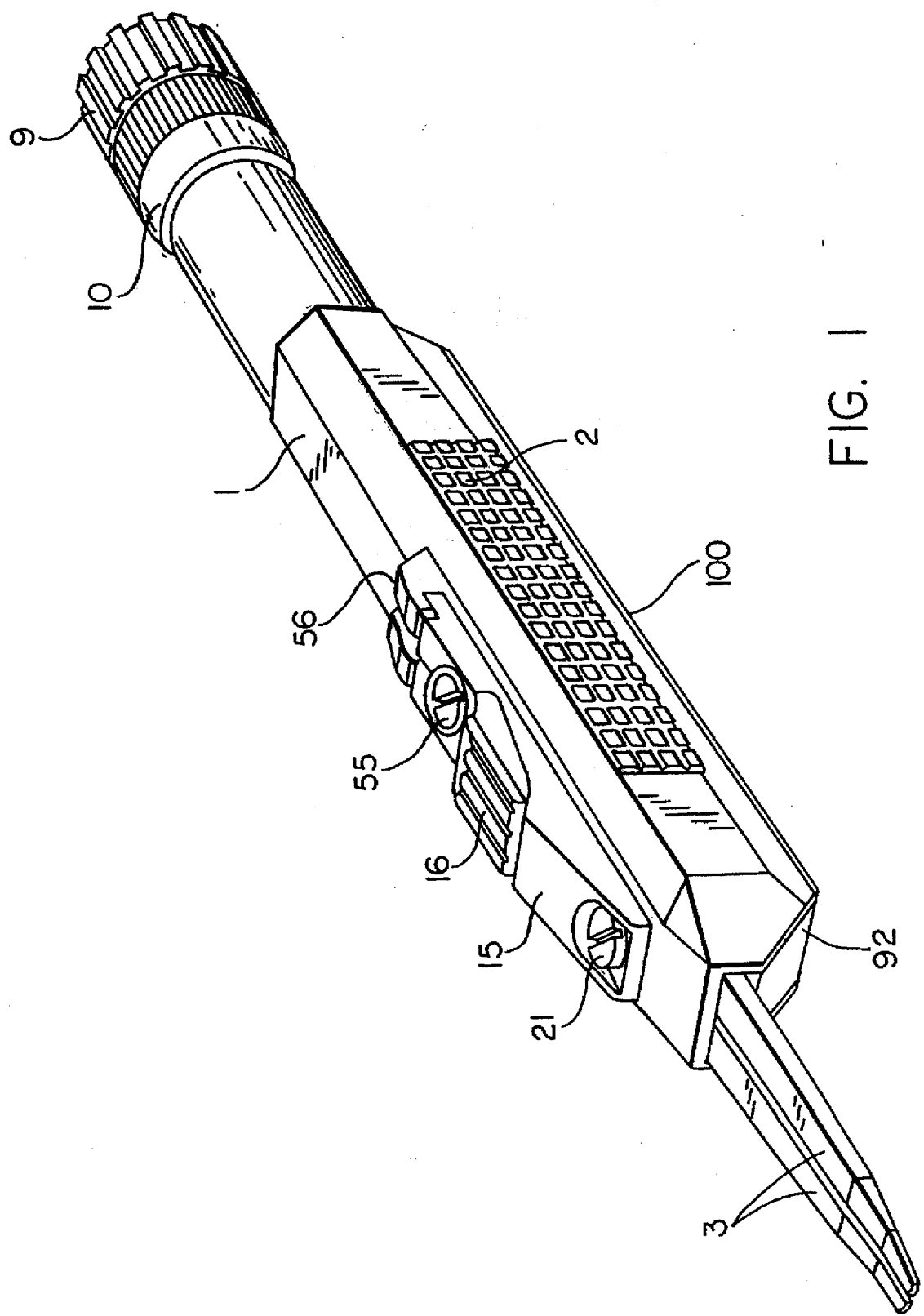
FIG. 1 shows a general perspective view of the gripper according to the invention.
Figure 2:
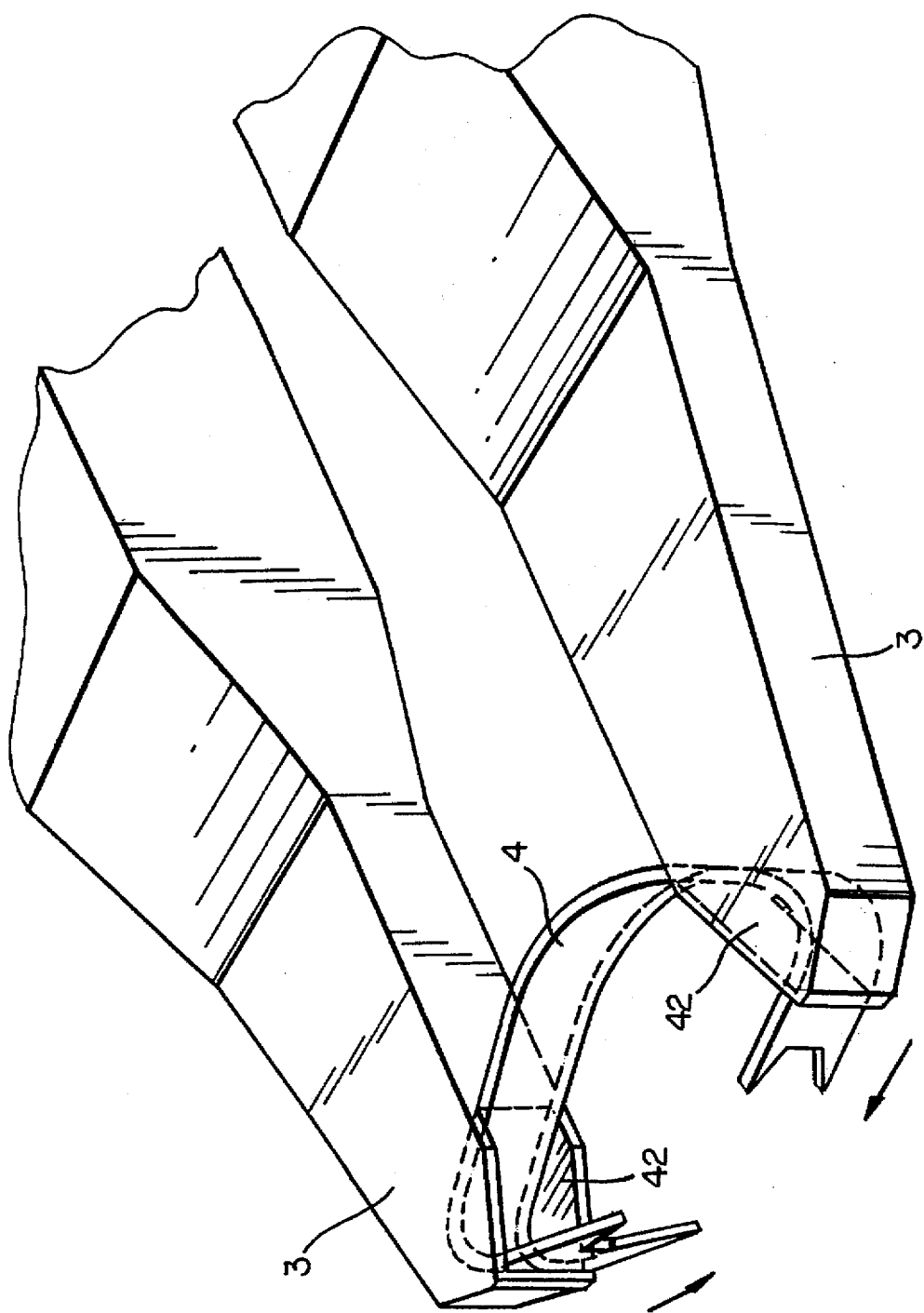
FIG. 2 is an enlarged view showing the jaws of the gripper holding a staple to be fastened.

Situated at the front upper portion and inside the sleeve are mechanisms having the following functions:

A) A mechanism in the casing 15 (FIG. 4) which is controlled by pressure applied by the operator's index finger on index finger operated lever 16 which drives a staple crimping device arranged on a displaceable sliding member or a longitudinally movable piece 17 responsive to index finger lever via coupling or inner articulated lever 18 (FIGS. 4, 16, 17). This casing is fastened on the sleeve 1 by the key bolt 19 which is inserted in keyway 20 and by screw 21 which is screwed onto sleeve 1 (FIGS. 1, 4). The small casing 15 can easily be removed from the sleeve 1 by loosening screw 21 so that the internal mechanisms may be disassembled and removed (FIGS. 1, 4).

B) Within the sleeve 1, plate 13 supports the gripper system, i.e., its two arms 3 and the mechanism controlling the feeding of staples to the gripper (FIGS. 4, 5, 6, 7, 9, 10).

Figure 12:
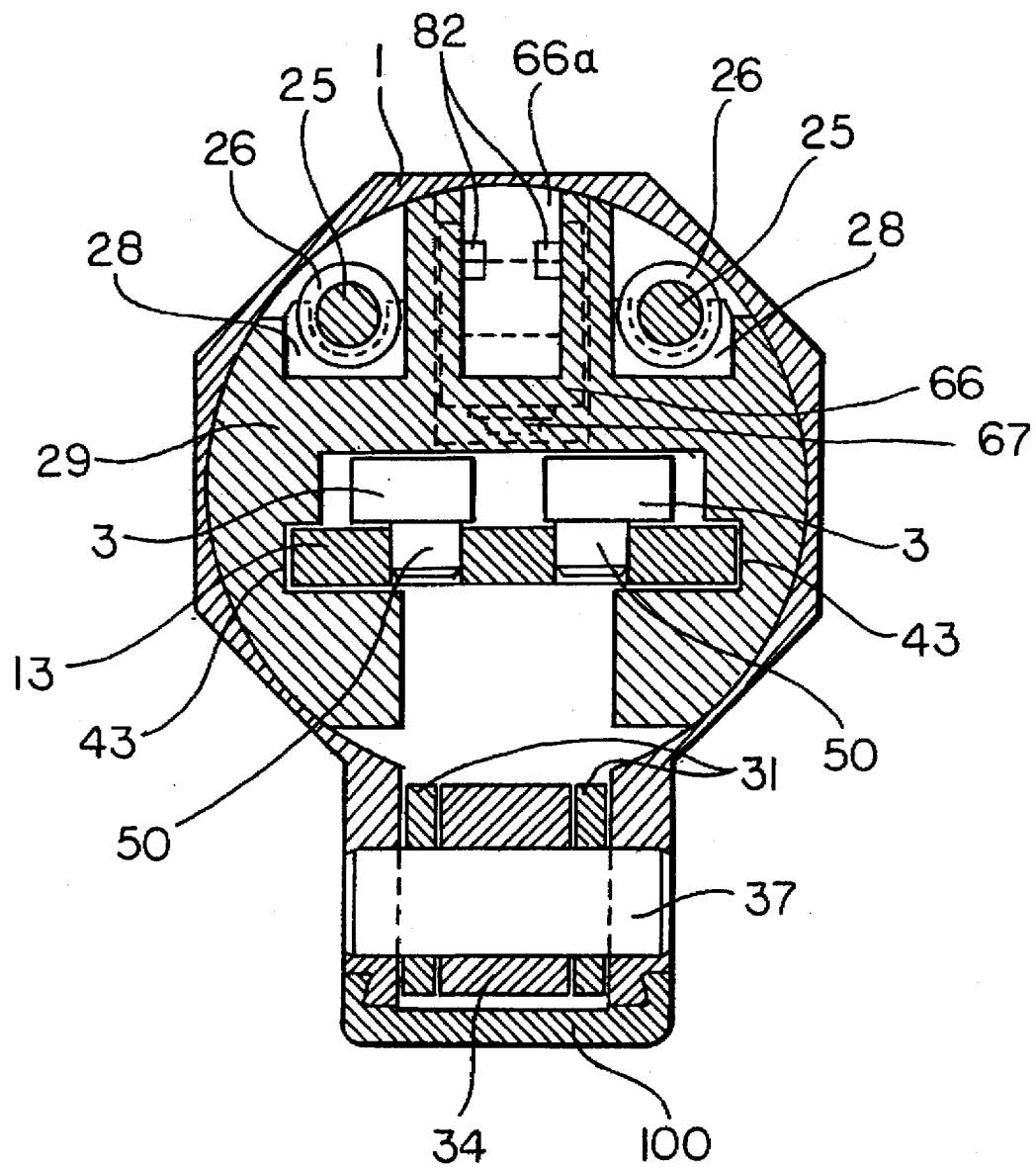
FIG. 12 is a cross-sectional view of the gripper.

C) A mechanism located above the plate 13 serves to place a new staple in the arms of the gripper (FIGS. 4, 5, 6). The horizontally movable part of this mechanism is shown in a plan view in FIG. 11. In FIG. 11, pieces 22, 23, 24 are integral with two tie rods 25. The bushes 26 and piece 27 slide on the tie rods 25. The bushes 26 support two springs 27a and are pressed against portion 28 of the body 29 (FIGS. 4, 12). The springs 30 push piece 27 against the bushes 26.

D) A rocker arm 31 is located below the plate 13. The front portion 31a of the rocker arm 31 receives a magazine 32 carrying a quantity of staples 33 and its central portion receives a staple push-rod 34 (FIGS. 4, 5, 6, 7, 8, 9, 10). The cam 35 of piece 36 controls the rocker arm 31 in such a way that the latter brings the magazine and the supply of staples contained therein into the position where a new staple can be supplied (FIGS. 5, 6). The rocker arm 31 and the push-rod 34 (which acts as an articulated lever) swivel about the axle 37 fastened within the lower portion of the sleeve 1 (FIGS. 4, 5, 6, 12).

E) Inside the sleeve 1 at the rear, two levers 38 (FIGS. 7, 8, 9, 10) pivot about their axles 39 causing the two arms 3 of the gripper to close around the staple 4 by means of two small fingers or projections 41 of piece 36 when the knob 9 is moved back toward the front opposite the direction indicated by arrow 40 (FIGS. 7, 8, 9, 10). The staple is now held in the sockets 42 (FIG. 2) which are shaped in such a way that the staple conforms to the configuration of sockets 42 and is securely held therein (FIGS. 7, 8, 10).

Mechanisms B, C, E are mounted on the body 29 (FIGS. 4, 5, 6, 12) outside the sleeve and then the entire arrangement is inserted into the central bore of the sleeve 1 (FIG. 12) via the rear opening. The body 29 is then locked in place by the back cover 11 and nut 10 which is screwed onto the body 29. The body 29 has grooves 43, the plate 13 being driven so as to slide therein by means of rod 14 and knob 9 which the operator manipulates for reloading the gripper (FIGS. 7, 8, 10, 12). In the working position (placement of staple), the two arms 3 of the gripper project out at the front of the sleeve through an opening provided for this purpose.

When the knob 9 is released from the bayonet locking system, the operator can pull back the knob and, via rod 14, drive the plate 13 which slides in the grooves 43 (FIGS. 5, 12). The arms 3 then occupy their interior or retracted position in which they can receive a new staple (FIGS. 4–9).

The gripper and its various mechanisms, described above, operate in the following manner:

1. Crimping the staples

With a staple 4 held in the sockets 42 of the arms 3, the operator attaches the staple by its claws 6 to the tissues of the vessels to be sutured (FIG. 13). Holding the gripper in the manner of a pen, the operator then applies pressure with the index finger on the index finger lever 16 located on top of the sleeve at the front (FIGS. 1, 4). Due to the position of the lever 16, the pressure to be applied and the short stroke required, the staple can be crimped without interfering with the exact positioning of the staple, the index finger of the operator resting in a natural position with the hand motionless.

The pressure applied to the lever 16 causes the coupling lever 18 which couples the longitudinally movable piece 17 to index finger lever 16 to rotate about its axle so that longitudinally movable piece 17 moves in a straight line toward the rear of the gripper (FIGS. 4, 16) while compressing the blade of the return spring 44 (FIG. 4). A pivot 45 is provided for each of the arms 3. Before the operator applies pressure and the rearward movement begins, the two pivots 45 each of which are integral with one of the arms 3 of the gripper are fixed in position between outer faces 46 of inner cam member piece 47 and an inner face 48 or on each of outer pieces or outer cam members 147 (FIGS. 16, 17). The outer faces 46 of inner piece 47 and inner faces 48 of outer pieces 147 provide for a pair of guide paths 49 for pivots 45 between inner piece 47 and each of the outer pieces 147. The position of the outer ends of the gripper arms corresponds to FIG. 13.

When the arrangement formed by outer pieces 147 and 47 and index lever piece 17 is displaced toward the rear, the pivots 45 follow the relative paths 49 provided on each side of piece 47. The arms 3 and pivots 45 themselves are not displaced along with these pieces since they are retained by plate 13 which remains in the position shown in FIG. 7. In FIG. 16, the line indicating the relative movement as defined by paths 49 shows that the inclined planes 47a of inner piece 47 cause the pivots 45 to move apart at first during the initial phase of displacement and the front ends of the arms 3 to move together, the latter pivoting about their axles 50 supported in plate 13 (FIGS. 7, 14, 16). The front ends of the arms 3 now occupy the position shown in FIG. 14, which shows that the crimping of the staple 4 has been effected by this movement. Continuing along each relative path 49, it will be seen that there is a central zone where the pivots do not move, followed by a final zone where the relative displacement defined by each of the paths 49 causes the pivots 45 to move together due to the diagonal portion of the faces 48 of each outer piece 147 (FIG. 16). The front ends of the arms 3 are then spread apart in the position shown in FIG. 15.

The two arms 3 are now located at a distance from the staple 4 so that the operator may retract the gripper without touching or tearing out the staple which has just been placed while maintaining pressure with the index finger on index finger lever 16. The operator can then release the pressure exerted by the index finger. A new staple can then be placed immediately in the arms of the gripper.

2. Presetting the crimping of the staple

It is useful for different kinds of sutures to possess the ability to modify the manner in which the claws of the staple are pressed together and thus to vary the crimping of the staple. A device shown in FIG. 17 is provided for this purpose. Inner piece 47 which is arranged on longitudinal movable piece or a displaceable sliding member 17 can also slide vertically according to arrow 51 (FIG. 16) so as to be guided by the cylinder 52. A spring 53 tends to move inner piece 47 away from longitudinally movable piece 17 (FIG. 17). Pin 54 limits this movement. Accordingly, piece 47 is pressed against the button 55 by spring 53. The button 55 which is supported in the sleeve 1 (FIG. 1) is locked by a safety screw 56 (FIGS. 1, 16, 17). When the screw 56 is released, the button 55 may be rotated in the direction of arrow 57 or in the opposite direction. The helical fluting 58 then effects a change in the vertical position of button 55 and inner piece 147 relative to piece 17 by moving it toward or away from the latter.

The inclined planes 59 of piece 47 will then alter the relative paths 49 by compelling the pivots 45 to spread apart to a greater or lesser extent according to the vertical position of inner piece 47. Accordingly, the crimping of the staple 4 can be varied by varying the degree to which the front ends of the arms 3 are moved together. Thus, the operator may vary the crimping of the staple by rotating the button 55. The operator then locks the safety screw 56. In this way, all of the staples placed by the operator will be crimped in the same manner.

3. Loading a new staple a) operation

The following steps must be performed in order to advance a new staple into sockets 42:

Knob 9 (FIG. 1) is unlocked in order to disengage the pins 12 from the bayonet grooves 60 by turning the knob in the direction of arrow 61 (FIG. 4).

With one hand holding the gripper, the other hand draws back the knob 9 in the direction indicated by the arrow (FIG. 5). The rod 14 then appears and the two arms 3 of the gripper withdraw into the interior of the sleeve (FIGS. 5, 8).

Toward the end of the pulling movement, the operator senses a slight increase in pulling effort. By continuing to pull back, the operator reaches the end of the stroke according to arrow 40 (FIGS. 6, 9).

The operator then pushes the knob 9 and accordingly the rod 14 toward the front again (FIGS. 6, 10). At the end of this forward movement, the operator relocks the knob 9 in the bayonet locking system by turning it in the opposite direction indicated by arrow 61 so that it engages smoothly. A new staple is now positioned between the arms 3 of the gripper (FIG. 10).

This movement is simple and fast and may be performed by an assistant.

b) operation of staple reloading mechanism

When the knob 9 and rod 14 are drawn back, plate 13 abuts against the back cover 11 (FIGS. 5, 8). Shortly before this, the shoulder 63 of piece 36 engages piece 27 and, in so doing, the tie rods 25 which are driven by the pressure of springs 30 (FIG. 5). Piece 22 which is integral with the tie rods 25 is likewise displaced toward the rear so as to compress the springs 27a which are less powerful than springs 30 (FIGS. 5, 11). During this displacement, the inclined surface 64 of piece 22 presses the inclined surface 65 of piece 66 along with its pivot 67 down into its seat 66a (FIGS. 5, 9).

During the displacement of plate 13, the inclined surface 68 of piece 36 which is supported by plate 13 (FIG. 5) pushes the cam 69 of piece 34 downward which causes the other end of piece 34 to rise (FIG. 5). As a result of the pressure applied by spring 70 on the crosspiece 71 associated with piece 31, the front end of piece 31 carrying the magazine 32 positions this magazine, i.e., its strip of staples 33, exactly opposite the pivot 67 of piece 66 (FIGS. 5, 9) so that the two pieces are pressed against one another.

By continuing to pull back in the direction indicated by arrow 40 with a slight increase in force, piece 36 slides toward the rear on plate 13 while compressing springs 30 and 72 (FIGS. 6, 10). The cam 35 of piece 36 pushes cam 69 of piece 34 downward still farther (FIG. 6). The lever 31 which is stopped by piece 66 cannot be further displaced, but piece 34 may still be displaced further by continuing to compress spring 70. The front arm of piece 34 which supports the blade of spring 73 is displaced and the blade is pressed below the washer 74 which makes up part of the magazine 32 (FIG. 6).

When the plate 13 supporting the arms 3 is displaced toward the rear, the faces 75 of the arms located at the rear of these arms encounter cams 38 which causes the front ends of the arms 3 to move apart (FIGS. 7, 8). This leaves open a free space level with these arms so that the pivot 67 and magazine with its store of staples 33 can position themselves therein as described above.

The staples, section 76 and pivot 67 are so dimensioned that the staples gently grasp these pieces. The staples can slide along these sections.

The pushing force exerted under the washer 74 by the leaf spring 73 lifts the entire stack of staples along section 76 and a staple 4 is engaged on the pivot 67, the height of the latter being equal to the width of a single staple. Thus, a single staple will be placed on this pivot 67 (FIGS. 5, 6, 9, 19). The operator then ceases to pull back on the knob 9 and the knob 9, rod 14 and piece 36 are pushed back toward the front by springs 30 and 72 (FIGS. 6, 10). Piece 36 slides toward the front on plate 13 and, in so doing, causes the cam 69 to rise again and the leaf spring 73 to drop. The stack of staples is no longer pushed upward. Piece 36 then continues to move forward and the lever 31 resumes its initial lower position (FIG. 4).

Figure 18:
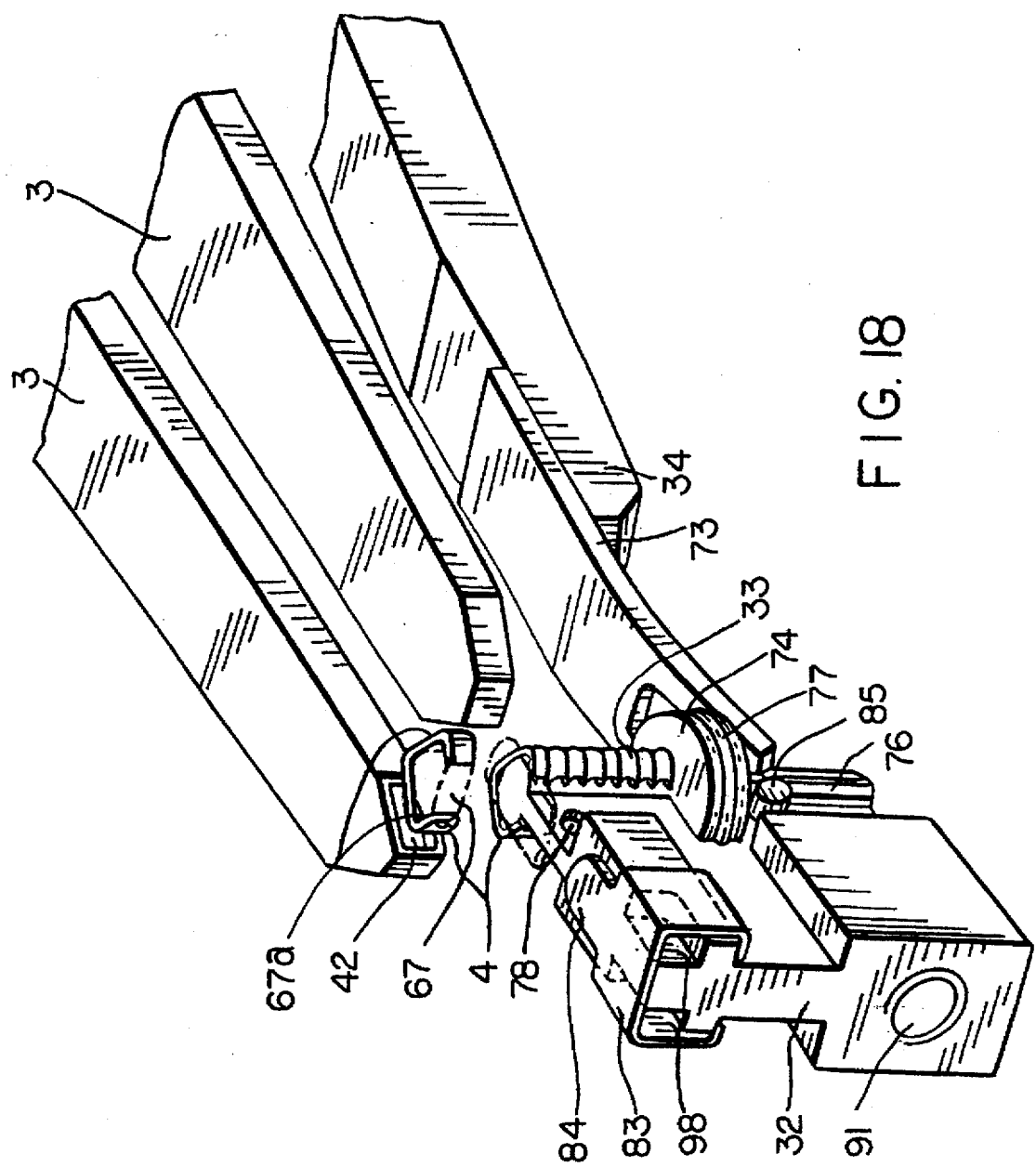

The washer 74 is provided with an annular spring 77 which engages in a groove constructed in the washer 74 as will be seen from FIGS. 8 and 18. This small spring, which is pretensioned in such a way that its ends exert pressure on section 76 serves to retain the washer 74 (FIG. 18) by holding it in the position into which it has been pushed by the leaf spring 73. When the last staple has been pushed onto the pivot 67, the two ends of the spring 77 engage in recess 78, thus locking the washer 74 on section 76 so that the washer 74 cannot be lost inside the gripper (FIG. 18).

Figure 19:
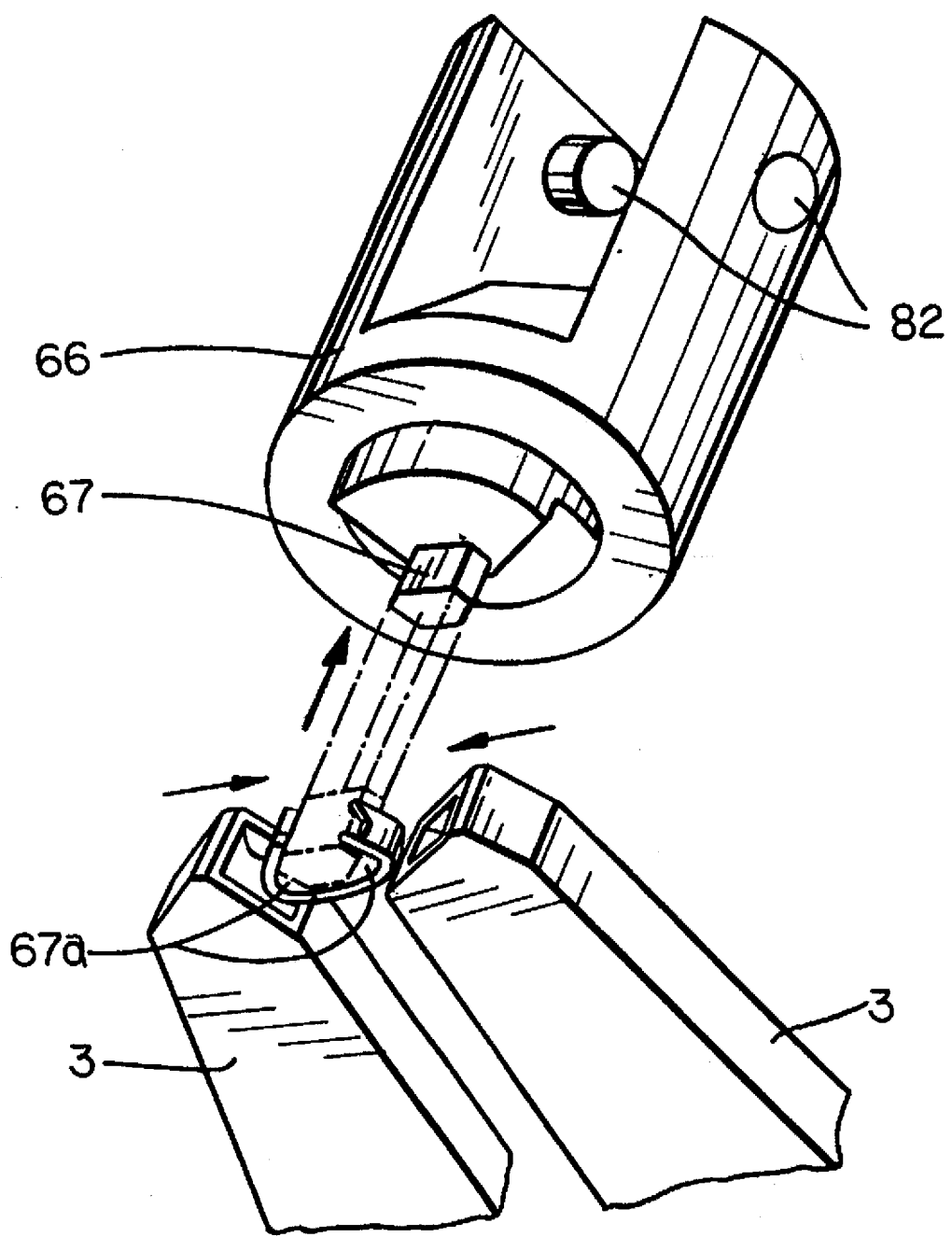

The contour of the pivot 67 is shown in FIGS. 18 and 19. It has undercuts or reliefs 67a allowing the arms 3 of the gripper to close around it, the staple being enclosed in the sockets 42 provided in these arms. This closing of the arms 3 for grasping the staple is effected via the projections 41 which slide in a bore hole constructed in piece 36 (FIG. 7). These two projections are pushed by a spring 79 and held in place by pins which are not shown in this drawing (FIGS. 7, 8). During the displacement of plate 13 and piece 36 toward the rear, the two projections are pushed back into their seat while passing along the inclined planes of the cams 3 (FIG. 8). Subsequently, during this same displacement, they resume their initial positions in the rear recess of the cams 38 according to FIG. 10. When the operator pushes the knob 9 and rod 14 forward again, the projections 41 pass under the inclined surface 80 of cams 38 and cause them to rock upward (FIG. 9) so as to compress the return springs 38a. The faces 75 of the arms 3 are now no longer pressed against the cams 38 (FIG. 9) and the arms 3 which are repelled by springs 81 spread apart and occupy the position shown in FIG. 10. The front ends of the arms 3 accordingly grasp the staple 4 positioned on the pivot 67 and the staple is now seated in the sockets 42 (FIGS. 8, 10, 18, 19).

As its forward displacement continues, piece 36 and its shoulder 63 allow the spring 27a to push piece 22 back into its initial position with reference to FIG. 4. This causes piece 66 to be lifted from its seat 66a again in that the inclined surface 64 acts on pins 82 (FIG. 4). The pivot 67 is lifted again along with piece 66 and the staple sliding on its profile remains held in the sockets 42 (FIGS. 8, 10, 19). The cams 38 have resumed their initial positions, having been pushed back by springs 38a, since the projections 41 holding the cams in the raised position are likewise displaced toward the from along with piece 36.

The operator continues to push the knob 9, rod 14, plate 13 and arms 3 toward the front and piece 36 resumes its initial location on plate 13. Springs 30 press piece 27 against bushes 24 and spring 72 presses piece 36 into its initial position on plate 13. The plate 13 itself is then carried toward the from and also resumes its initial position. The arms of the gripper carrying a new staple once more project out in front of the sleeve 1. The operator then locks the knob 9 in the bayonet locking system and the gripper is ready to place a new staple.

4. Changing the magazine

Figure 20:
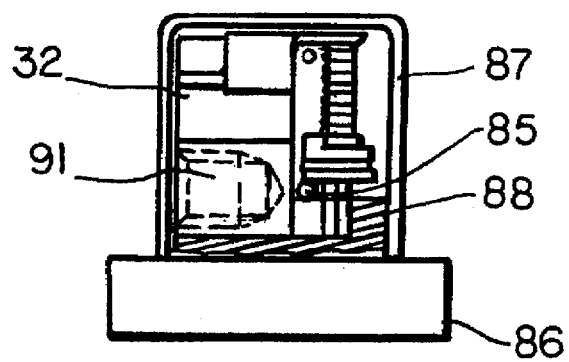
Figure 21:
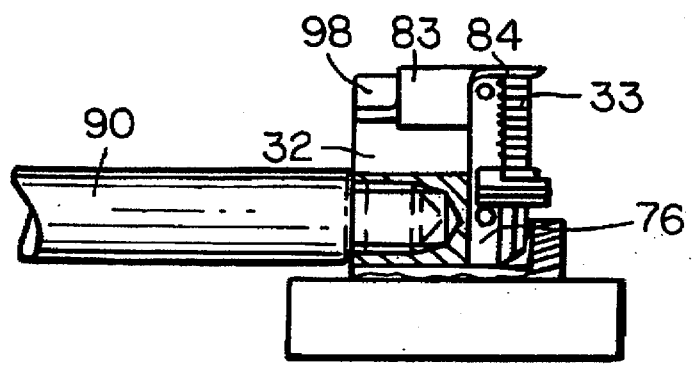
Figure 22:
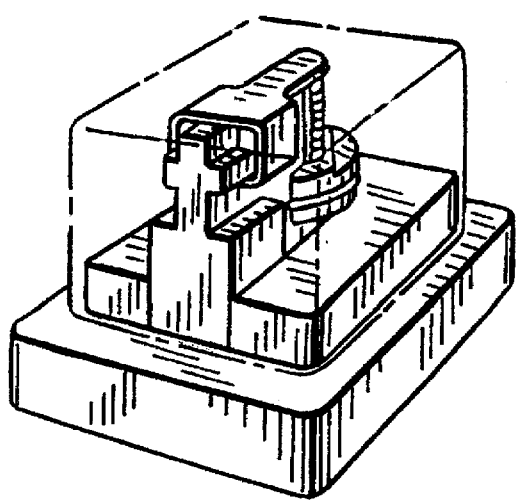

As will be seen from FIG. 18, magazine 32 comprises a section 76, a washer 74 being inserted on the latter. A stack of staples is placed on top of the washer 74. A clip 83 which slides on the upper portion of magazine 32 prevents the stacked staples from escaping from section 76 by means of its tongue or tab 84 (FIGS. 18, 21, 22, 23, 26, 27). In the storage and transport position, the clip 83 is arranged in such a way that its tab 84 covers the top of section 76 (FIGS. 20–22). The washer 74 abuts against a pin 85 in the opposite direction (FIGS. 18, 20, 21). Accordingly, the staples cannot be lost since they are locked by the tab 84 and washer 74.

As will be seen from FIGS. 20, 21, 22, the magazine 32 is placed on a base 86, e.g., a plastics base, for handling and transporting and is covered by a cover which can be made from the same material and can also be transparent, this base and cover making up its packaging. The base and cover are held together, for example, by a clamping arrangement 88 provided at their junction point. The magazine which is furnished with staples is placed in this package after cleaning, e.g., by ultrasound. The cover is then put in place and the entire package can easily be sterilized, e.g., by gamma radiation. A plurality of magazines could also be packaged together in a more substantial package.

Figure 23:
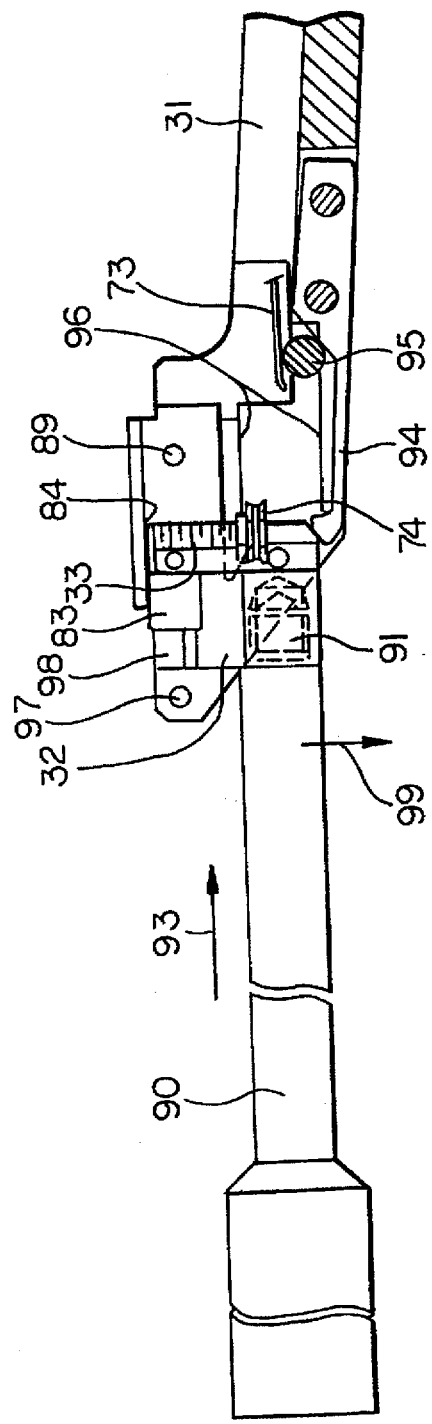

In order to insert the magazine into the gripper, the operator screws a spindle 90 (FIG. 23) into an internal thread 91 (FIG. 18) while holding the base 86 in his/her hand after removing the cover 87 so as to avoid contact between the magazine 32 and the operator's fingers. The operator detaches the magazine from its base by means of the spindle 90 and inserts it into the space 31a of the magazine support lever 31 inside the front portion of the sleeve 1 (FIG. 4). For this purpose, the operator uses the spindle 90 to place the magazine in the space 31a provided at the front of the lever 31 and pushes in the direction indicated by arrow 93 (FIG. 23).

As a result of this pushing, the pins 89 (FIG. 22) retain the clip 83 and cause it to slide along the magazine 32 into a position where its tab 84 releases the top of the stack of staples 33 allowing this stack to be lifted along section 76 when pushed via the washer 74 and leaf spring 73 during the reloading movement (FIG. 25). This same pushing movement in the direction of arrow 93 bends the spring 94 downward (FIG. 25) allowing the magazine 32 to pass through until abutting against pin 95.

The operator then unscrews the spindle 90 while maintaining a slight pressure on the magazine allowing the spring 94 to return to its initial position and retain the magazine 32 by its vertical face (FIG. 25).

After withdrawing the spindle, the cover 92 is put back in place and the gripper is ready for operation.

Figure 27:
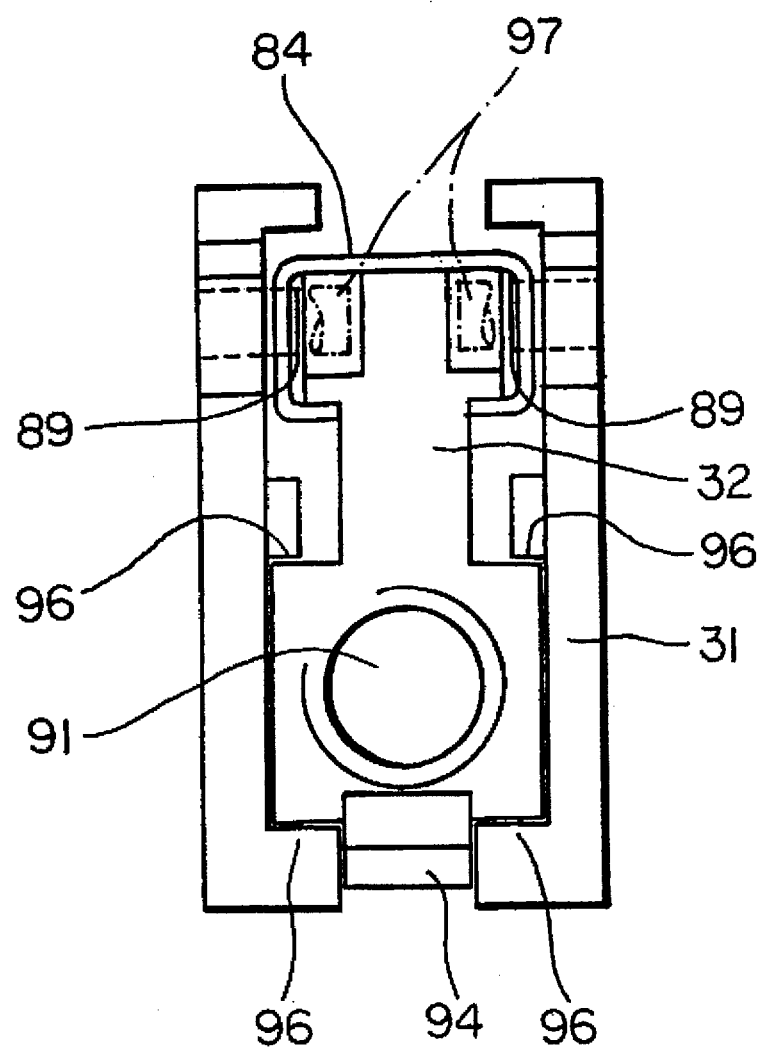

The magazine is securely held in place by shaped portions 96, pin 95 and the shoulder of spring 94 (FIGS. 23, 25, 27).

To extract the magazine when empty or at the conclusion of the operation, the cover 92 is removed and the spindle 90 is screwed into the internal thread 91 of the magazine 32 which is still positioned in the sleeve 1, i.e., in its receptacle 31a (FIG. 25). The shoulder of the spring 94 is pushed back by the outer diameter of the spindle when the latter is screwed into the internal thread 91 and spring 94 is bent downward so that it no longer retains the magazine. The operator can then extract the magazine from its receptacle by pulling in the opposite direction of arrow 93a (FIG. 25).

Figure 24:
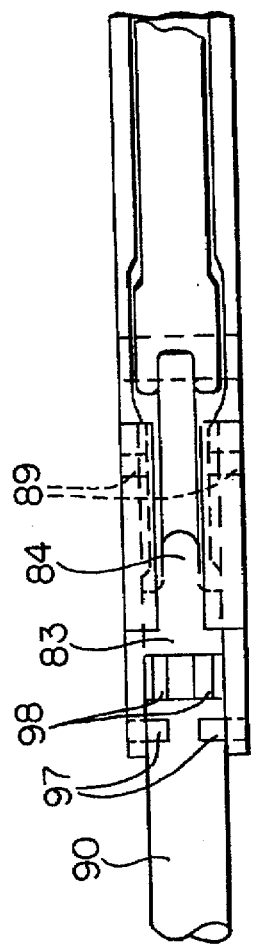

During this extracting movement, the clip 83 is held back at the end of the movement in that it abuts against pins 97 as shown in FIGS. 26 and 27. As the operator continues the extracting movement, the clip 83 slides along the magazine 32 and its tab 84 once more covers the top of the stack of staples 33. In this way, the staples cannot be lost should any staples remain on the profile 76 of the magazine. The movement for extracting the magazine is terminated when the pins 97 abut against the end of the recess 98 (FIGS. 24, 26). The operator then detaches the magazine in the direction of arrow 99 (FIG. 23) by means of spindle 90 and removes the magazine from the gripper.

If any staples remain on the magazine, the operator replaces the magazine on its base 86, removes the spindle 90 by unscrewing it, and replaces the cover 87 on the base. The entire package can be resterilized if necessary. If all of the staples have been used, the spindle is unscrewed and the magazine is disposed of.

Piece 100 is a cover closing the lower surface of the sleeve. It is held in place by a dovetail assembly sliding along the sleeve and can be removed if necessary (FIGS. 1, 4, 12).

I claim:

1. A device for microanastomosis of blood vessels comprising:

a housing including a sleeve (1) having two oppositely disposed open ends;

a drive plate (13) slidable within said sleeve (1) and supporting an axle (50);

a pair of retractable, movable arms (3) supported and articulated on said axle (50) and each said arm having one end extending outside of said sleeve (1) through one of said two oppositely disposed open ends;

a rod (14) operatively coupled with said plate (13), and a gripper coupled with one end of said rod (14), each of said movable arms (3) having, at a front end thereof, a socket (42) for grasping and holding a staple (4) between said movable arms in each said socket, one end of said rod being positioned at a rear portion of said housing opposite to said one of said oppositely disposed ends for movement of said plate (13), and extending outside of said sleeve (1) through the other of said oppositely disposed open ends opposite to said one open end and axially aligned therewith;

a removable magazine (32) receivable within said sleeve (1) and supported on said plate (13) for storing staples prior to their being grasped by said sockets (42);

means for effecting a grasping of said staple (4) including means for moving said rod (14) in a first direction out of said sleeve (1) through said other of said oppositely disposed open ends, and moving each said socket (42) to a position facing the staple (4) in said removable magazine (32) and movement of said rod (14) includes means for displacement of each of said arms (3) for movement of said arms (3) apart from each other to move each said socket (42) into position to face the staple (4);

said means for moving said rod (14) including means for displacement of said rod (14) in a second direction opposite to said first direction for movement of said rod (14) into said sleeve (1) towards said one open end to move each said socket (42) by movement of the arms (3) into a work position for crimping said staple (4) onto a blood vessel;

means including a finger operated lever (16) external of said sleeve (1) for moving said arms towards each other for effecting a preset movement of said arms (3) together by moving said arms towards each other to effect a crimping of the staple responsive to ends of the arms (3) being moved together towards each other;

a displaceable sliding member (17) internal of said sleeve (1) acting on an inner articulated lever (18), an inner cam member (47) supported on said displaceable sliding member (17), said inner articulated lever (18) being rotatable and operatively associated with said displaceable sliding member (17) for the displacement of said sliding member (17), said inner cam member (47) having a pair of outer cam faces (46), a pair of outer cam members (147) each having an inner cam face (48) cooperating with one of said outer cam faces (46) each said arm (3) having pivots (45) integral therewith and fixed in position between one of said outer cam faces (46) provided on said inner cam member (47), and one of said inner cam faces (48) and one of said outer cam members (147) having shaped lateral faces (48) thereon; said inner cam member (47) having inclined planes (47a) for producing a relative movement (49) relative to each said pivot (45) of each said arm (3) for causing said pivots (45) to move apart initially during an initial phase of displacement and each said front end of each of said arms (3) being provided with said socket (42) to move together for crimping of the staple, and after the staple has been crimped, said arms (3) move apart for release of the staple (4) from each said socket (42) and allow each said socket (42) to be withdrawn and to accept a new staple.

2. The device for microanastomosis of blood vessels according to claim 1, comprising:

means including said inner cam member (47) slidable on a slidable member (17) for presetting the degree of bending or crimping, and said inner cam member (47) being slidable on a cylinder (52);

a button (55) forming a continuation of said cylinder (52), and being provided laterally with a helical groove (53) for receiving an end of an adjustable safety screw (56) integral with said sleeve (1), said inner cam member (47) being provided with inclined faces or planes (59); and means for rotating said button (55), including means for adjusting or loosening said safety screw (56) and positioning said inclined faces (59) of said inner cam member (47) relative to said pivots (45) for displacing from each other said front ends of the arms (3) having said sockets (42) holding the staple (4) for releasing the staple from the sockets (42).

3. The device for microanastomosis of blood vessels according to claim 2, including:

means in said sleeve (1) responsive to the retraction of said arms for holding a removable staple magazine (32) in a front portion (31a) of a rocker arm (31) integral with an articulated lever (34) having a front end and a rear end, said front end being closer to a front end of said housing than said rear end so that said sockets (42) grasp a staple (4) after said arms (3) have been moved apart, said lever (34) including a cam (69) and said rocker arm (31) including a leaf spring (73) responsive to said lever (34);

a piece (36) supported on said plate (13) having a rear inclined surface (68) and a front cam (35);

means for swivelling said rocker arm (31) and said lever (34) including drawing said plate (13) back together with said piece (36) so that said rear inclined surface (68) pushes said cam (69) downwardly causing the rear end of said lever (34) to rise; and means responsive to positioning of said cam (69) contacting said front cam (35) for controlling said leaf spring (73) holding a stack (33) of staples in position.

4. The device for microanastomosis of blood vessels according to claim 1, wherein each end of legs (5) of the staple (4) has a pair of claws (6).

5. The device as claimed in claim 1, including a bayonet locking system comprising:

a rotatable knob (9) for drawing said arms (3) into said sleeve (1) in a first direction and pushing said arms (3) in a second direction opposite to said first direction for securement of a staple between said arms; and and pins (12) engageable in grooves (60), said knob (9) being rotatable in a first direction for unlocking said rod for withdrawal of said arms and being rotatable in the opposite direction after a staple is grasped between said arms for locking said knob.

6. The device as claimed in claim 1, including a leaf spring (73) cooperating with a washer (74) for lifting an entire stack of staples, and a pivot (67) for receiving a staple to be grasped by said sockets (42).

7. The device as claimed in claim 6, wherein said washer (74) is provided with a groove for receiving an annular spring (77) for holding said washer (74) in the position pushed by said leaf spring (73), and said spring (77) locks said washer (74) on a section (76) to prevent loss of said washer inside said gripper.

8. The device as claimed in claim 6, wherein said pivot (67) is provided with undercuts (67a) about which said arms (3) close.

9. The device as claimed in claim 1, wherein said magazine is provided with an internal thread 91, and including a spindle having an external thread receivable within and cooperating with said internal thread for holding the magazine for insertion into said gripper.

10. The device as claimed in claim 9, including safety means comprising pins (97) abutting against a clip (83) for causing said clip (83) to slide along said magazine (32) to release a top of a stack of staples, and tab (84) covering the top of the stack of staples to prevent any loss of staples remaining on a profile (76).

11. The device as claimed in claim 1, including means for crimping all staples uniformly, comprising said inner cam member (47) having inclined planes and means including the pivots (45) to alter the relative position between said sliding member (17) and said inner cam member (47).

* * * * *